US006952606B2

United States Patent
Anderson et al.

(10) Patent No.: US 6,952,606 B2
(45) Date of Patent: Oct. 4, 2005

(54) COMBINED ELECTRICAL IMPEDANCE AND ULTRASOUND SCANNER

(75) Inventors: Roselle Anderson, Solna (SE); Thomas Mertelmeier, Erlangen (DE); Bernhard Scholz, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 445 days.

(21) Appl. No.: 10/202,871

(22) Filed: Jul. 26, 2002

(65) Prior Publication Data

US 2003/0028092 A1 Feb. 6, 2003

(30) Foreign Application Priority Data

Jul. 26, 2001 (DE) .......................... 101 36 529

(51) Int. Cl.[7] ............ A61B 5/05; A61B 10/00
(52) U.S. Cl. ..................... 600/547; 128/916
(58) Field of Search .................... 600/547, 548, 600/506, 530, 407, 160, 182, 437, 438; 324/600; 128/916, 915

(56) References Cited

U.S. PATENT DOCUMENTS

| 5,787,889 A | | 8/1998 | Edwards et al. |
| 5,935,066 A | * | 8/1999 | Harris .................... 600/436 |
| 6,560,480 B1 | * | 5/2003 | Nachaliel et al. ........... 600/547 |
| 6,678,552 B2 | * | 1/2004 | Pearlman .................... 600/547 |
| 6,725,087 B1 | * | 4/2004 | Rubinsky et al. ........... 600/547 |
| 6,807,444 B2 | * | 10/2004 | Tu et al. .................... 600/547 |

FOREIGN PATENT DOCUMENTS

DE      101 02 204      7/2001

* cited by examiner

*Primary Examiner*—Daniel Robinson
(74) *Attorney, Agent, or Firm*—Young & Thompson

(57) ABSTRACT

An electrical impedance scanner having a probe in its contact surface [lacuna] an electrode matrix for detection of the surface distribution of the body current and/or body potentials originating from an opposing electrode which is fitted at some other point on the body of the patient, in which case additional ultrasound transducers (12) for the transmission and reception of ultrasound waves are installed in the contact surface (9) of the probe (3) and are connected to an ultrasound investigation appliance which has a monitor.

18 Claims, 3 Drawing Sheets

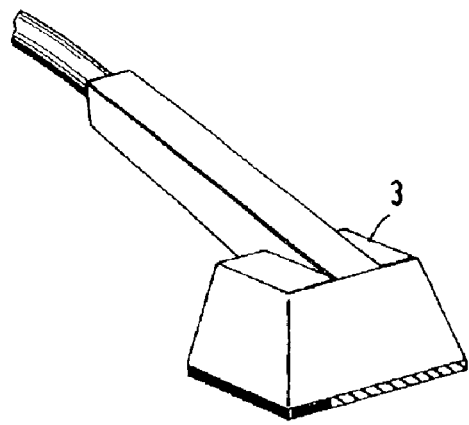
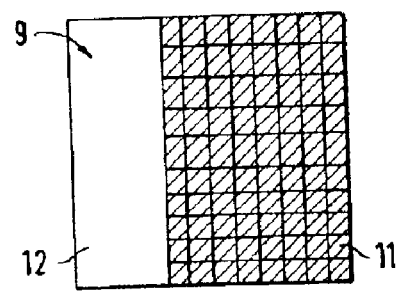
FIG. 2          FIG. 3
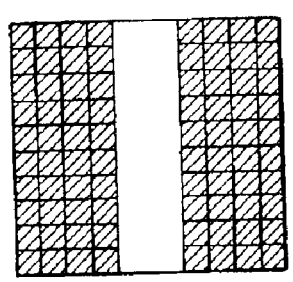
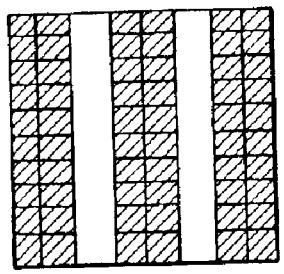
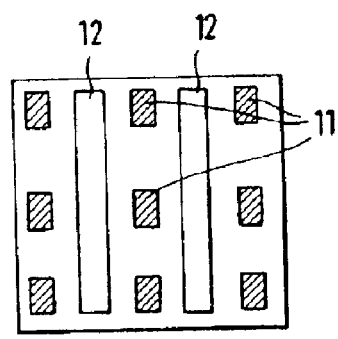
FIG. 4          FIG. 5          FIG. 6
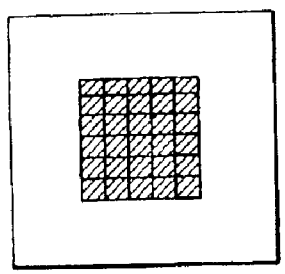
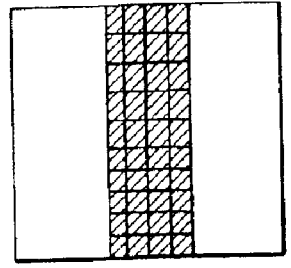
FIG. 7          FIG. 8

US 6,952,606 B2

COMBINED ELECTRICAL IMPEDANCE AND ULTRASOUND SCANNER

FIELD OF THE INVENTION

The invention relates to an electrical impedance scanner having a probe in its contact surface [lacuna] an electrode matrix for detection of the surface distribution of the body current and/or body potentials originating from an opposing electrode which is fitted at some other point on the body of the patient.

BACKGROUND OF THE INVENTION

An impedance scanner of the type mentioned initially is known from DE 101 02 204 A1. Electrical impedance scanners such as these are based on the knowledge that malignant tumors have different impedance characteristics than the healthy surrounding tissue so that, when a weak AC voltage ($\leq 5$ V) is applied to, or a weak alternating current ($\leq 4$ mA) is introduced into, the body by means of the opposing electrode, this changes the electrical field in the region of a tumor, so that this results in a corresponding change in the current density and potential distribution on the skin surface under the probe with the electrode matrix.

By way of example, with an ultrasound appliance as is described in U.S. Pat. No. 5,787,889, an ultrasound record is generally also made in advance or subsequently for more detailed interpretation of the investigation result of such electrical impedance measurements, and this is primarily used to exclude cysts and to localize lesions for biopsy. The ultrasound investigation is itself less specific for the investigation of benign and malignant lesions.

It is not only time-consuming to carry out different investigations successively, but this also has the disadvantage that the association of the results that are in each case found, that is to say the comparability of the respective locations of a problem that has been found, requires further considerable effort.

SUMMARY OF THE INVENTION

The invention is thus based on the object of refining an electrical impedance scanner of the type mentioned initially such that an ultrasound investigation can also be carried out in a simple manner and with the measurement results easily being associated with one another.

According to the invention, this object is achieved in that additional ultrasound transducers for the transmission and reception of ultrasound waves are installed in the contact surface of the probe and are connected to an ultrasound investigation appliance which has a monitor. In this case, it is preferably intended to be possible to display the results of both investigation systems, that is to say of the electrical impedance measurement and of the ultrasound investigation, on one monitor at the same time, for which reason the electronics for both investigation systems should expediently be combined in one appliance.

In this case, the ultrasound transducers may be arranged at the side alongside the electrode matrix or else—which improves the image correlation of the two investigation systems even further—be arranged in cutouts in the electrode matrix of the probes, for example by choosing a coarser grid for the electrode distribution.

BRIEF DESCRIPTION OF THE DRAWINGS

Further advantages, features and details of the invention will become evident from the following description of an exemplary embodiment and from the drawing, in which:

FIG. 2 shows a view of the probe with ultrasound transducers arranged at the side alongside the electrode matrix, FIG. 3 shows a plan view of the contact surface of the probe as shown in FIG. 2, FIGS. 4 to 8 show plan views of the contact surface of a combined electrical impedance/ultrasound probe, in each case with a modified distribution of the electrodes and of the ultrasound transducers.

DETAILED DESCRIPTION OF THE INVENTION

Figure 1:
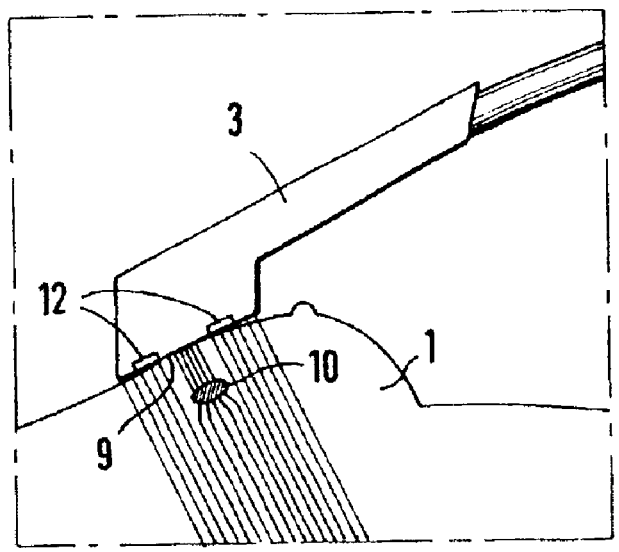
FIG. 1 shows a schematic illustration of a breast investigation using a combined impedance/ultrasound scanner according to the invention.
Figure 1:
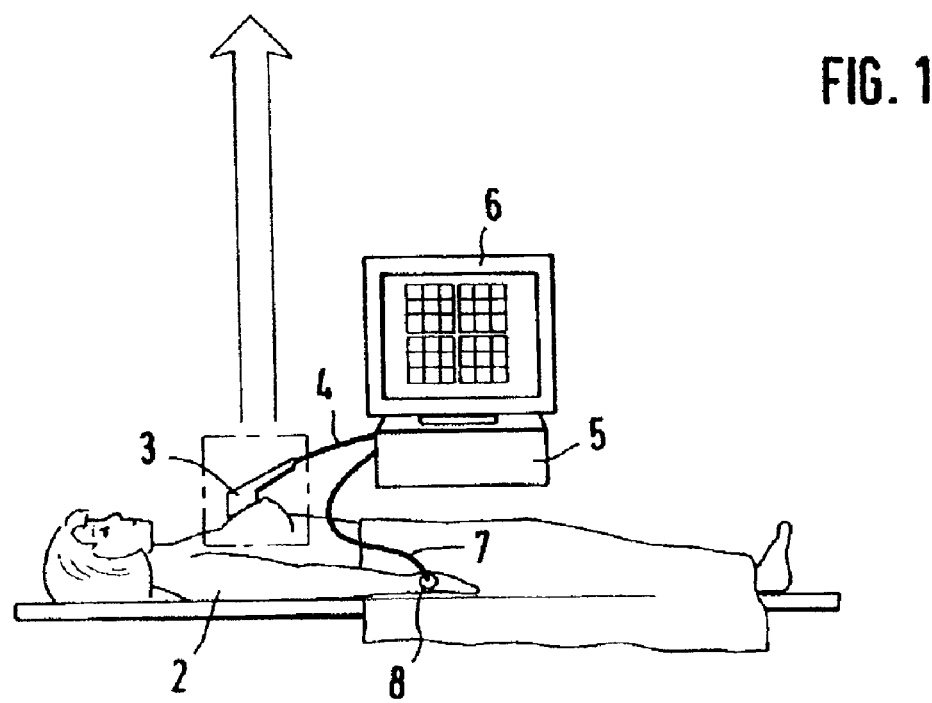

FIG. 1 shows, schematically, the investigation of the breast 1 of a female patient 2 by applying and moving a probe 3, which is connected via a cable 4 to the electronics 5 of an electrical impedance scanner, which has an associated monitor 6. A second cable 7 leads from the electronics to an opposing electrode 8 which, by way of example, the female patient 2 holds in her hand. The upper part of FIG. 1 shows, schematically and enlarged, how the currents which run from the opposing electrode 8 through the body to the probe 3, which has an electrode matrix 3, are changed by a tumor 10, whose conductivity differs from that of the healthy surrounding tissue, and are partially concentrated, so that, from the distribution of the surface current/surface potential it is possible to trace a malign change in the tissue directly or indirectly by conversion by means of an equivalent circuit, in order to allow a distribution of conductance and capacitance values across the electrode matrix of the probe 3 to be displayed on the screen 6.

According to the invention, not only are the electrodes of an electrode matrix 11 installed in the contact surface 9 of the probe 3, but also ultrasound transducers as well, in which case these ultrasound transducers, of which at least one is used for the transmission of ultrasound waves and one for the reception of ultrasound waves, can be arranged in different ways. In FIGS. 3 to 8, the fields for the electrodes for electrical impedance measurement and spaces in between, in which the ultrasound transducers for the ultrasound investigation can be arranged, can be seen, in the form of dark shaded areas. In this case, it is advantageous for the combined investigation method for the injection of the ultrasound waves into the tissue and for the process of ensuring that there is good conductivity from tissue to electrodes to be ensured using the same mechanism, that is to say using a gel.

Figure 9:
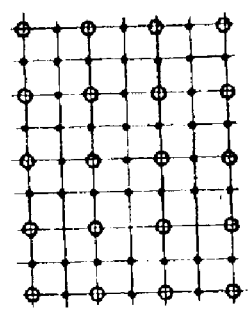
FIG. 9 shows an illustration of a fine electrode grid and of a coarse electrode grid.
Figure 10:
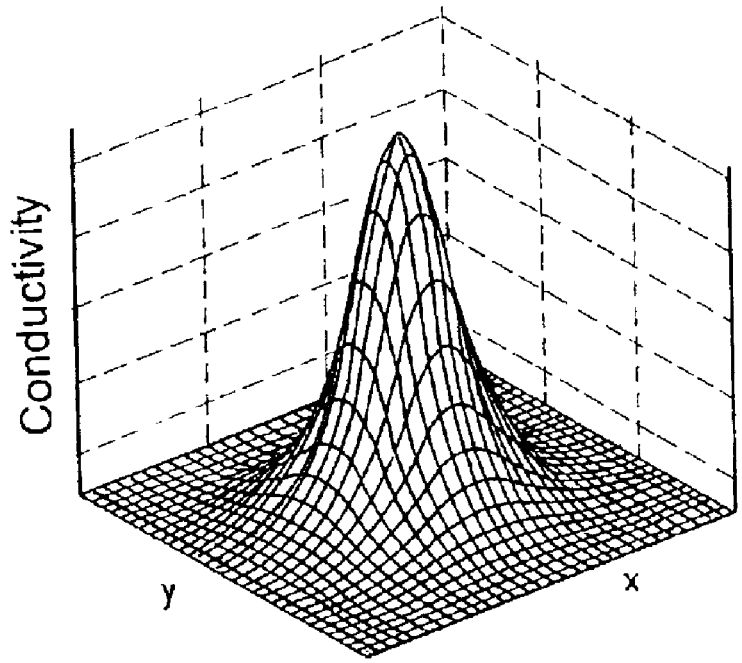
FIGS. 10 and 11 show illustrations of the three-dimensional current distribution during the electrical impedance measurement of a tumor with a fine electrode distribution (FIG. 10) and with an electrode distribution with a coarse grid (FIG. 11).
Figure 11:
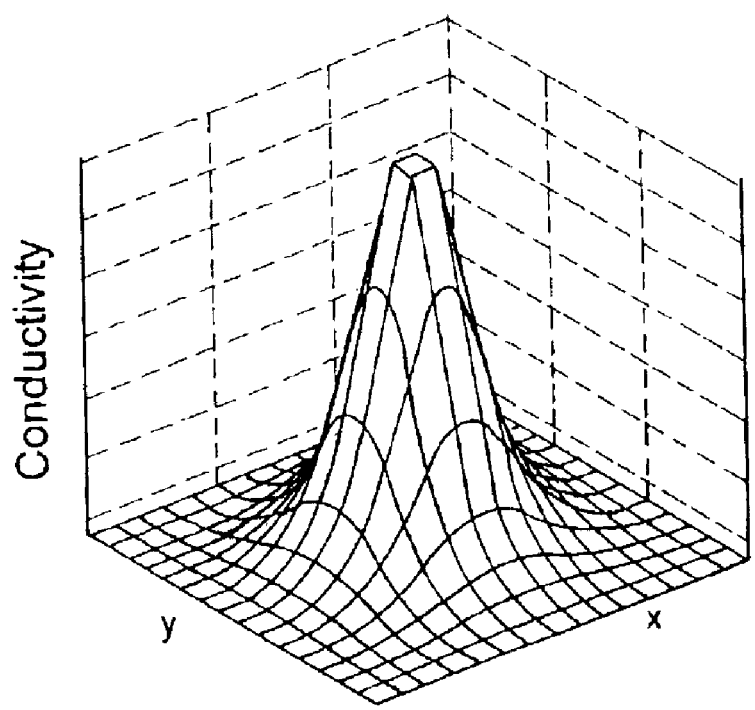

FIGS. 9 to 11 show the result of the simulation calculations, from which it is possible to see that the expedient thinning of the electrodes in order to create space for the accommodation of the ultrasound transducers leads to only a minor adverse effect on the position resolution. In this case, FIG. 10 shows the simulated conductance distribution as can be measured at all the intersection points as shown in FIG. 9 using an existing electrical impedance system with a fine electrode matrix. FIG. 11 shows the analogous distribution of the conductivity, but with only 25% of the electrodes, so that space is created between them for ultrasound transducers. The signal from the simulated tissue inhomogeneity in FIG. 11 is essentially the same as that in FIG. 10.

The ultrasound transducers 12 are connected to the electronics 5 via the same cable 4 as the electrodes for the electrical impedance measurement, with the electronics of both investigation systems being combined in these electronics 5. The results of both investigations can be displayed on the same monitor 6, thus considerably simplifying the problem of registration of the two data records for image fusion. This in turn simplifies the localization of the lesion for any possible biopsy, thus improving not only the sensitivity but also the specificity.

The use of ultrasound for finding purposes and electrical impedance measurement in order to distinguish between benign and malignant tissue results in a considerable improvement in the workflow in an investigation. At the same time, the combined appliance is also cheaper than the total amount for an ultrasound appliance and an electrical impedance appliance, and can be used more easily and better. Only one modality can in each case also be operated on its own, of course, with the other being switched on by pushing a button. Investigations of the thyroid gland, of the lymph nodes, of the blood vessels and of the prostate etc., represent a further major field of use of a combined electrical impedance/ultrasound scanner according to the invention.

What is claimed:

1. An electrical impedance scanner having a probe in its contact surface [lacuna] an electrode matrix for detection of the surface distribution of the body current and/or body potentials originating from an opposing electrode which is fitted at some other point on the body of the patient, characterized in that additional ultrasound transducers (12) for the transmission and reception of ultrasound waves are installed in the contact surface (9) of the probe (3) and are connected to an ultrasound investigation appliance which has a monitor.

2. The electrical impedance scanner as claimed in claim 1, characterized in that the ultrasound transducers (12) are arranged at the side, alongside the electrode matrix (11).

3. The electrical impedance scanner as claimed in claim 1, characterized in that the electrode matrix (11) has cutouts in which the ultrasound transducers (12) are installed.

4. The electrical impedance scanner as claimed in claim 1, wherein the electrical impedance scanning function and the ultrasound scanning function (EI and US) can selectively be operated either individually or combined.

5. The electrical impedance scanner as claimed in claim 1, characterized by a picture-in-picture display with both the electrical impedance scanning function and the ultrasound scanning function being carried out at the same time.

6. The electrical impedance scanner as claimed in claim 1, characterized in that the results of the electrical impedance scanning function and the ultrasound scanning function can be displayed at the same time on one monitor (6) by means of image fusion.

7. The electrical impedance scanner as claimed in claim 1, characterized in that the electronics for the electrical impedance scanning function and the ultrasound scanning function are combined in one appliance (5).

8. The scanning device of claim 1, wherein both the electrode matrix and the ultrasonic transducers are arranged on one said surface of the probe such that the scanning device can be used with the probe surface positioned on skin of a patient.

9. A scanning device comprising:

an electronics unit comprising an ultrasound analyzer and an electrical impedance analyzer;

a probe comprising ultrasound transducers and an electrode matrix, both the ultrasound transducers and the electrode matrix being disposed on a single contact surface of the probe;

means for transmitting ultrasound data and electrical impedance data from the probe to the ultrasound analyzer and electrical impedance analyzer, respectively, in the electronics unit; and an opposing electrode;

wherein the electrode matrix is structured and arranged to detect current from the opposing electrode and generate the electrical impedance data, the ultrasound transducers being structured and arranged to transmit and receive ultrasound waves and generate the ultrasound data.

10. The scanning device of claim 9, wherein the ultrasound transducers and the electrode matrix are arranged on the probe surface so that all of the ultrasound transducers are arranged in a single group disposed adjacent a single group of all of the electrode matrix.

11. The scanning device of claim 9, wherein the ultrasound transducers and the electrodes in the electrode matrix are arranged on the probe surface so that all of the ultrasound transducers are arranged in a single band disposed between first and second bands of the electrodes.

12. The scanning device of claim 9, wherein the ultrasound transducers and the electrodes in the electrode matrix are arranged on the probe surface in alternating bands.

13. The scanning device of claim 9, wherein the ultrasound transducers are arranged in bands on the probe surface, the electrodes in the electrode matrix being arranged on the probe surface in groups separated by the bands of the ultrasound transducers.

14. The scanning device of claim 9, wherein the electrodes in the electrode matrix are arranged in a single group, with the ultrasound transducers being arranged on the probe surface to surround the single group of electrodes.

15. The scanning device of claim 9, wherein the ultrasound transducers and the electrodes in the electrode matrix are arranged on the probe surface so that all of the electrodes are arranged in a single band disposed between first and second bands of the ultrasound transducers.

16. The scanning device of claim 9, wherein the device is user-controllable to selectively enable only the ultrasound transducers, only the electrodes, or both the ultrasound transducers and the electrodes.

17. The scanning device of claim 9, further comprising a monitor connected to the electronics unit, the electronics unit being constructed and arranged to simultaneously display on the monitor a representation of both the ultrasound data and the electrical impedance data.

18. The scanning device of claim 9, wherein the electrode matrix and the ultrasonic transducers are arranged on the surface of the probe such that the scanning device can be used with the probe surface positioned on skin of a patient.

* * * * *

UNITED STATES PATENT AND TRADEMARK OFFICE
CERTIFICATE OF CORRECTION

PATENT NO. : 6,952,606 B2 Page 1 of 1
APPLICATION NO. : 10/202871
DATED : October 4, 2005
INVENTOR(S) : Anderson et al.

It is certified that error appears in the above-identified patent and that said Letters Patent is hereby corrected as shown below:

Column 3, claim 1, cancel "(12)", "(9)" and "(3)"; claim 2, cancel "(12)" and "(11)"; claim 3, cancel "(11)" and "(12)"; claim 6, cancel "(6)"; claim 7, cancel "(5)".

Signed and Sealed this

Twentieth Day of March, 2007

JON W. DUDAS
*Director of the United States Patent and Trademark Office*